United States Patent [19]

Stoll et al.

[11] Patent Number: 5,308,512

[45] Date of Patent: May 3, 1994

[54] THIODIGLYCOL ALKOXYLATE DERIVATIVES, A PROCESS FOR THEIR PRODUCTION AND THEIR USE AS FABRIC SOFTENERS

[75] Inventors: Gerhard Stoll, Korschenbroich; Peter Daute, Essen; Ingo Wegener; Faize Berger, both of Duesseldorf, all of Fed. Rep. of Germany

[73] Assignee: Henkel Kommanditgesellschaft auf Aktien, Duesseldorf, Fed. Rep. of Germany

[21] Appl. No.: 961,683

[22] PCT Filed: Jun. 28, 1991

[86] PCT No.: PCT/EP91/01213

§ 371 Date: Mar. 5, 1993

§ 102(e) Date: Mar. 5, 1993

[87] PCT Pub. No.: WO92/00959

PCT Pub. Date: Jan. 23, 1992

[30] Foreign Application Priority Data

Jul. 7, 1990 [DE] Fed. Rep. of Germany ....... 4021694

[51] Int. Cl.$^5$ ............................................. D06M 10/08
[52] U.S. Cl. .................................... 252/8.7; 252/8.6; 252/8.9; 568/27; 568/28; 554/227; 560/263; 560/264
[58] Field of Search ................ 560/263, 264; 554/227; 568/27, 28; 252/8.6, 8.7, 8.9

[56] References Cited

U.S. PATENT DOCUMENTS 4,830,636 5/1989 Horodysky ........................... 44/70

FOREIGN PATENT DOCUMENTS 0176797 4/1986 European Pat. Off. .
2334899 1/1974 Fed. Rep. of Germany .
3604039 8/1987 Fed. Rep. of Germany .
3833076 4/1989 Fed. Rep. of Germany .
3936862 5/1991 Fed. Rep. of Germany .
4010606 10/1991 Fed. Rep. of Germany .
0213067 12/1983 Japan .
153309 3/1984 Japan .
1097396 1/1968 United Kingdom .

OTHER PUBLICATIONS

Trofimov, Zh. Prikl. Khim., vol. 48, pp. 626–628 1975.
Vogel & Krüssman & Seifen, Öle, Fette, Wachse, vol. 115, 1989, pp. 3–8 Article Unavailable.
J. Falbe, Surfactants in Consumer Products, Springer, 1987, pp. 87–90.
Vogel & Krussmann, Seifen, Öle, Fette, Wachse, vol. III, 1985, pp. 567–574 1985.

Primary Examiner—Paul Lieberman
Assistant Examiner—Michael P. Tierney
Attorney, Agent, or Firm—Ernest G. Szoke; Wayne C. Jaeschke; Real J. Grandmaison

[57] ABSTRACT

The process of producing alkoxylated thiodiglycol sulfoxide derivatives and thiodiglycol sulfone derivatives corresponding to formula I

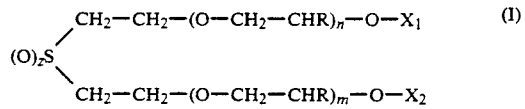

wherein $X_1$ and $X_2$ may be the same or different and represent a hydroxyl-substituted aklyl radical containing 8 to 30 carbon atoms, an acyl radical of an alkyl monocarboxylic acid containing 8 to 30 carbon atoms, and $X_1$ or $X_2$ may be hydrogen, R represents hydrogen or methyl, z is 1 or 2, n is 0 to 25 and m is 1 to 25, by reacting an alkoxylated thiodiglycol with a $C_8$14 $C_{30}$ α-olefin expoide or a $C_8$–$C_{30}$ monocarboxylic acid in a molar ratio of about 1:1 to about 1:2, and oxidizing the mono- and bis- ethers or mono- and bis- esters formed to the sulfoxide or sulfone derivatives.

6 Claims, No Drawings

THIODIGLYCOL ALKOXYLATE DERIVATIVES, A PROCESS FOR THEIR PRODUCTION AND THEIR USE AS FABRIC SOFTENERS

BACKGROUND OF THE INVENTION

1. Field of the Invention

This invention relates to new thiodiglycol alkoxylate derivatives, to their production by reaction of thiodiglycol with alkylene oxides, subsequent reaction with α-olefin epoxides or monocarboxylic acids and oxidation with hydrogen peroxide to form the corresponding mono- and/or bis-ethers or mono- and/or bis-esters of thiodiglycol alkoxylate sulfoxides or sulfones and to the use of the thiodiglycol alkoxylate sulfoxides or sulfones as fabric softeners.

Hitherto, considerable practical significance has been attributed to quaternary ammonium compounds, particularly dimethyl distearyl ammonium chloride, in the field of domestic and institutional fabric softeners (see P. Vogel and H. Kru⊕mann, Seifen, ole, Fette, Wachse, Vol. 111, pages 567 to 574, 1985 and L. Godefroy and H. Hein, Seifen, ole, Fette, wachse, Vol. 115, pages 3 to 8, 1989).

In view of the increasing consideration being given to the storability and viscosity characteristic and also to the biodegradability of highly concentrated fabric softeners, numerous proposals for replacing these components by nitrogen-free substitute compounds or corresponding systems have been published. These proposals encompass both inorganic components, more particularly inorganically insoluble components, such as layer silicate compounds (see for example DE-PS 23 34 899), and also selected organic components, for example disalts of long-chain α-sulfofatty acids and combinations of such systems (see DE-PS 36 04 039).

2. Discussion of Related Art

Thiodiglycol derivatives, a process for their production and their use as fabric softeners are already known from the teaching of applicants' German patent application P 39 36 862.9. However, in view of their limited solubility in water and their high melting points, the compounds in question can only be formulated as expensive mixtures in stable dispersions.

Accordingly, the problem addressed by the present invention was to provide a hitherto unreported class of nitrogen-free inorganic compounds for use as rinse cycle fabric softeners which, on the one hand, would be easier to formulate through greater dispersion stability and, on the other hand, would be distinguished by better feel behavior compared with the compounds described above.

DESCRIPTION OF THE INVENTION

Other than in the operating examples, or where otherwise indicated, all numbers expressing quantities of ingredients or reaction conditions used herein are to be understood as modified in all instances by the term "about".

In a first embodiment, therefore, the present invention relates to new alkoxylated thiodiglycol sulfoxide derivatives or thiodiglycol sulfone derivatives corresponding to general formula I

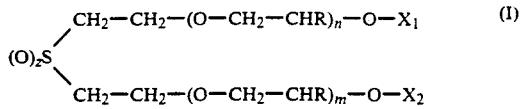

in which $X_1$ and $X_2$ may be the same or different and have the following meanings:

hydroxyl-substituted alkyl radicals containing 8 to 30 carbon atoms, acyl radicals of alkyl monocarboxylic acids containing 8 to 30 carbon atoms;

one of the substituents $X_1$ or $X_2$ may be hydrogen,

R is hydrogen and/or methyl, z is the number 1 or 2, n is a number of 0 to 25 and m is a number of 1 to 25.

The thiodiglycol alkoxylate compounds of general formula (I) according to the invention are a hitherto unreported class of compounds. They are prepared by reaction of alkoxylated thiodiglycol compounds with α-olefin epoxide compounds containing 8 to 30 carbon atoms in the molecule or by the corresponding reaction of alkoxylated thiodiglycol compounds with alkyl monocarboxylic acids of comparable chain length and subsequent oxidation with hydrogen peroxide to the corresponding sulfoxides or sulfones.

According to the invention, the alkoxylated thiodiglycol compounds are obtained by the base-catalyzed reaction of thiodiglycol with alkylene oxides. The alkoxylation is generally carried out by the method known from the literature for alcohols at a reaction temperature in the range from about 100 to 200° C., under a pressure of 1 to 50 bar and in a nitrogen atmosphere.

In one preferred embodiment of the invention, a catalytic quantity of methanolic potassium hydroxide solution is added to the thiodiglycol in an autoclave and the thiodiglycol is reacted with ethylene oxide at 140 to 150° C. to form the ethoxylated thiodiglycols, the pressure not exceeding $5 \times 10^5$ Pa.

According to the invention, the molar ratio of thiodiglycol to alkylene oxide is between 1:1 and 1:25 and preferably between 1:1 and 1:10. The expert knows that the alkoxylation reaction can result in a homolog distribution with a varying distribution of the EO degree (see J. Falbe, "Surfactants in Consumer Products", Springer 1987, pages 87 to 90). In addition to basic catalysts, such as preferably potassium hydroxide or sodium methanolate, the cationic layer compounds known from DE-OS 38 33 076 and DE 40 10 606.3 may also be used as alkoxylation catalysts.

In one important embodiment of the invention, the corresponding mono- and/or bis-ethers of the alkoxylated thiodiglycol compounds corresponding to general formula (I) with β-hydroxyalkyl groups in $X_1$ or $X_2$ are formed by opening of the epoxide ring, depending on the molar ratio between the thiodiglycol alkoxylates and the α-olefin epoxide compound (1:1 to 1:2). By contrast, another route to the bis-ether derivatives of thiodiglycol is described in GB-PS 1,097,396. The starting compounds used there are divinyl sulfones and alcohols which do not lead to the β-hydroxyalkyl group according to the invention in the corresponding bis-[2-alkoxyethyl]-sulfones.

In one preferred embodiment of the invention, the thiodiglycol alkoxylates are reacted with the $C_{8-30}$ α- olefin epoxide compound in the desired molar ratio (1:1 to 1:2) by addition of a typical basic catalyst, such as for example an alkali metal hydroxide and/or alkali metal alcoholate, in a quantity of at least 0.05% by weight to about 5% by weight and preferably in a quantity of about 0.1 to 1% by weight, based on the total quantity weighed in.

The actual reaction takes place at temperatures of at least 100° C. to about 200° C. and preferably at temperatures of about 160 to 170° C. over a period of about 3 to 6 hours to an epoxide oxygen content below 0.5% and preferably below 0.3%. The epoxide oxygen content is used for continuous monitoring of the reaction and, ultimately, for determining the quantitative course of the reaction.

The reaction of the alkoxylated thiodiglycol compounds with the alkyl monocarboxylic acids or reactive derivatives thereof gives the corresponding compounds of the mono- and/or bis-ester type corresponding to general formula (I), depending on the molar ratio of the thiodiglycol compound to the alkyl monocarboxylic acid (1:1 to 1:2). A similar reaction has already been described in the Russian literature (V.A. Trofimov, I.N. Gurshko and V.I. Isagulyants, Zh. Prikl. Khim., Vol. 48, pages 626 to 628, 1975). According to this literature reference, however, pure thiodiglycol is reacted with acid chlorides in benzene in the presence of pyridine to form the corresponding bis-esters of thiodiglycol, subsequent oxidation with cumyl hydroperoxide in n-heptane leading to the sulfoxides.

The resulting reaction products of the mono- and/or bis-ether or mono- and/or bis-ester type of the alkoxylated thiodiglycol compounds are then oxidized in known manner, for example with a certain quantity of 15 to 70% and preferably 35 to 70% hydrogen peroxide, to form the sulfoxide ($z=1$ in general formula (I)) and/or with at least twice that quantity of hydrogen peroxide to form the sulfone ($z=2$ in general formula (I)). As known to the expert, the oxidation of mercapto compounds can lead—according to the reaction conditions—to mixtures of sulfides, sulfoxides and sulfones which also fall within the scope of the present invention. In principle, the oxidation of the alkoxylated thiodiglycol derivatives in accordance with the invention may be carried out both with hydrogen peroxide and with other typical oxidizing agents for mercapto compounds (see, for example, Houben-Weyl, Vol. E 11, pages 1194–1202). It can be of advantage to use carboxylic acids, preferably acetic acid, for the oxidation of the alkoxylated compounds of the ester type with hydrogen peroxide in accordance with the invention.

Within the comparatively broad range of new thiodiglycol derivatives according to the invention as defined by general formula (I), selected narrower subclasses are distinguished by particular suitability for use as fabric softeners in accordance with the present invention. In a preferred embodiment of the invention, therefore, the substituents $X_1$ and $X_2$ are derived from B-hydroxyl-substituted alkyl radicals or from acyl radicals containing 12 to 24 carbon atoms and, more particularly, approximately 12 to 18 carbon atoms. The preferred substituents of this type for $X_1$ and $X_2$ are corresponding straight-chain radicals.

Compounds of general formula (I), which are distinguished by the fact that different radicals of the described type are present in $X_1$ and $X_2$, so that corresponding mixed radicals of the type defined in accordance with the invention are present in the particular molecule, fall within the scope of the present invention. Structurally the same and, if desired, structurally different radicals may be present in $X_1$ and $X_2$. For reasons of easier accessibility alone, preference is attributed to structurally the same radicals which, in the case of compounds containing mixed radicals $X_1$ and $X_2$, will contain, for example, corresponding radicals differing in their chain length.

Thiodiglycol derivatives corresponding to general formula (I) which contain uniform radicals and, in particular, the same radicals, i.e. identical radicals of the particular type mentioned, may be of particular advantage for the purpose of fabric softening according to the invention. However, both in this embodiment and in the previously mentioned embodiment of the compounds with mixed radicals $X_1$ and $X_2$, the invention encompasses mixtures of different compounds corresponding to general formula (I). As described in detail hereinafter in connection with the use of these components for fabric softening, it can be particularly useful to employ certain selected mixtures of compounds corresponding to general formula (I) containing relatively long radicals in $X_1$ and $X_2$ with corresponding and, in particular, structurally identical components corresponding to general formula (I), but with shorter radicals in $X_1$ and $X_2$. The reason for this is that certain properties which are of technological significance in connection with fabric softening can be influenced through the specific character of the substituents $X_1$ and $X_2$. Accordingly, it is possible in accordance with the invention to use mixtures in which the individual components are optimized in a certain way in regard to a desirable performance profile, but are then combined with other components which in turn are selected and synthesized in a different way in regard to their performance profile.

The foregoing observations on the substituents $X_1$ and $X_2$ from the compounds corresponding to general formula (I) apply similarly to the possibility of combining the parameters z, i.e. to the choice of compounds of the sulfoxide type or sulfone type. In practice, the sulfones ($z=2$) can be of particular significance because compounds of this type are not endangered by disproportionation reactions such as can occur in principle with sulfoxide compounds. In addition to the sulfones with their neutral odor, the foul-smelling sulfides can be formed as a result of this disproportionation reaction. In principle, however, both the sulfones according to the invention and the sulfoxides can be perfumed with typical fragrances without suffering any significant reduction in their softening properties.

In its most important embodiment, the invention encompasses mixtures of fabric-softening agents which contain the alkoxylated thiodiglycol compounds of general formula (I) either as such or in admixture with dissolving, emulsifying and/or dispersing aids or with stabilizers. These auxiliaries used in addition to the compounds of general formula (I) may optionally have washing power and/or a detergency-boosting effect of their own.

The various possibilities afforded by the invention are illustrated in the following Examples which describe partial aspects of the inner core of the embodiment of the teaching according to the invention in question here. Compounds corresponding to general formula (I) of the bis-ether type, which contain β-hydroxyl-substituted linear alkyl radicals with 16 or 18 carbon atoms, develop excellent softening effects both in the form of the sulfone compound and in the form of the sulfoxide compound when applied via an aqueous auxiliary phase in rinse bath softening.

In one particularly important embodiment of the present invention, the ethoxylated thiodigycol compounds of the bis-ether type corresponding to general formula (I) with a substituent $X_1$ or $X_2$ derived from the $C_{16}$ α-olefin epoxide show particularly good feel and formulation properties. In the context of the invention, ethoxylated thiodiglycol compounds having an EO degree of 1 to 5 and preferably 1 to 2 show particularly favorable performance properties. The reasons for this narrow EO range lie on the one hand in the considerable increase in the hydrophilicity of the thiodiglycol compounds according to the invention with higher EO degrees, which leads to poorer feel properties, and on the other hand in the above-mentioned poorer formulation properties of the non-ethoxylated thiodiglycol compounds attributable to their pronounced hydrophobicity.

If corresponding α-hydroxyl-substituted $C_{18}$ derivatives or corresponding $C_{16}$ derivatives are used in the absence of auxiliaries, the treated fabric does not appear to undergo pronounced softening. However, if the component corresponding to general formula (I) used as softener is combined with dispersion or emulsification aids, for example of the anionic and/or nonionic surfactant type, and/or with emulsifiers, for example of the glycerol partial ether or glycerol partial ester type, the fabric-softening effects, for example in final rinse softening, are not only fully developed again, they can even clearly surpass the effect of the corresponding shorter-chain derivatives corresponding to general formula (I). In the last-mentioned case, therefore, the co-use of dispersion or emulsification aids has a distinct effect-enhancing influence. On the basis of this illustration, which is intended purely as an example, the expert can determine and formulate suitable or optimized mixtures by conducting simple preliminary tests.

In the course of the work culminating in the present invention, it was also found that the degree of dispersion or emulsification of the compounds corresponding to general formula (I) in the application state can have a critical influence on the effectiveness of the new class of compounds according to the invention as fabric softeners. It is important both to the absolute effect and to maintenance of the effect over prolonged periods, particularly in aqueous mixtures, to establish a high level of very fine emulsification or dispersion of the active substances which they will retain in storage. Two measures in particular are available for this purpose and may even be combined with one another, namely: using dispersion or emulsification aids in the preparation of the combinations, particularly aqueous combinations, of active substances and adopting a certain procedure in the production of the aqueous preparations. The following observations may be made in this regard:

The longer the chain length of the substituents $X_1$ and/or $X_2$ in the sulfone or sulfoxide (I) used, the greater the need for emulsifying and/or dispersing auxiliaries. Compounds containing more than 12 carbon atoms in the particular substituents $X_1$ or $X_2$ and particularly those in the $C_{16-18}$ range particularly effective for the purpose of fabric softening according to the invention generally require the co-use of such additional components in the mixture of active substances. In one important embodiment of the invention, the thiodiglycol compounds corresponding to general formula (I) are used in admixture with surface-active auxiliaries in cases such as these. Effective auxiliaries in this regard are surfactants in the broad sense. According to the invention, therefore, the thiodiglycol compounds may be mixed both with anionic surfactants and also with nonionic surfactant compounds. Suitable anionic surfactants are, for example, fatty alcohol sulfate salts and also alkyl sulfonate salts, preferably alkali metal and alkaline earth metal salts and, in particular, Na and Mg salts. Within the first group, tallow alcohol sulfate and related compounds are mentioned as a particularly suitable mixing component. The second group includes, for example, α-sulfofatty acid methyl ester sulfonates, disalts of α-sulfonated fatty acids and comparable compounds. Suitable nonionic components are both conventional oligoethoxylates of oleophilic components containing active hydrogen atoms and—in particular—the alkyl glycosides belonging to the class of nonionic surfactants. For the purpose of optimization in accordance with the invention, not only will the desired enhancement of the fabric-softening effect understandably be in the foreground, the general compatibility of the fabric treatment auxiliaries in particular will also be taken into consideration. Tallow alcohol sulfate, wetting or emulsifying alkyl glucoside compounds and/or disalts of α-sulfofatty acids with a wetting and emulsifying effect can therefore be particularly significant in this regard.

Another class of auxiliaries for the formulation of strong-acting, particularly aqueous, preparations of the compounds corresponding to general formula (I) are emulsifiers for maintaining the established state of fine emulsification or dispersion. Many compounds of this type are known to the expert. Particularly suitable emulsifiers for the purposes of the invention are, for example, glycerol partial ethers and/or glycerol partial esters which, in addition to one or two free hydroxyl groups, contain relatively long-chain hydrocarbon radicals in the ether- or ester-forming functional substituents.

In mixtures of alkoxylated thiodiglycol compounds of general formula (I) and auxiliaries of the type just mentioned the alkoxylated thiodiglycol compounds according to the invention may be present in quantities of 5 to 95% by weight (based on the mixture as a whole) and preferably in quantities of about 20 to 70% by weight. Mixing ratios of the sulfones and/or sulfoxides corresponding to general formula I to pronounced emulsification aids, more particularly surface-active types, of 1:5 to 5:1 and, more particularly, of the order of 1:2 to 2:1 may be used with advantage.

The second possibility mentioned above for enhancing the effect of the new compounds lies in the choice of particular working conditions in the production of the concentrates, particularly aqueous concentrates, of active substances for their subsequent dilution with more water for practical use in fabric softening. More particularly, two process parameters need to be taken into account in this regard:

To establish a particularly fine state of emulsification, it has proved to be useful to emulsify the optionally molten active substances or mixtures of active substances in aqueous phase at least room temperature to around 100° C. Thus, it can be useful initially to introduce the emulsification aid in an aqueous solution at 60 to 95° C. and to stir in the alkoxylated thiodiglycol compounds in solid form at the same temperature. It is important in this regard to mix the aqueous phase intensively with the active-substance phase containing optionally molten thiodiglycol compounds. It can also be useful to maintain intensive mixing during cooling of the aqueous concentrate to ambient temperature.

It has also been found to be particularly useful in cases where the thiodiglycol compounds of general formula (I) and the dispersing or emulsifying auxiliaries, for example of the tallow alcohol sulfate type, are used together initially to subject the mixture of active substances to intensive homogenization, particularly in the melt, and then to emulsify the mixture in the aqueous phase under the conditions described above. It is possible in this way to achieve particularly reliable fine emulsification and hence enhancement of the intended fabric-softening effect and, at the same time, to obtain concentrates of the mixture of active substances which remain stable in storage for prolonged periods.

In the preparation of the aqueous dispersions and/or emulsions, it is advisable to maintain active substance contents in the aqueous formulation initially produced in the range from about 1 to 50% by weight and preferably in the range from about 5 to 20% by weight. In the concentration in which the emulsions are used for fabric softening and, more particularly, for rinse cycle softening in institutional and domestic washing machines, the concentrates may be used in such quantities that the active substances or mixtures of active substances according to the invention are ultimately used in quantities of from about 0.05 to 2% by weight and, more particularly, in quantities of from about 0.1 to 1% by weight, based on fabric dry weight.

The formulation of the water-based fabric softeners as defined in accordance with the invention enables a relatively broad pH range to be established. Thus, the pH values of corresponding aqueous solutions may be in the range from about pH 4 to 11 and are preferably in the range from about pH 5 to 7.

In addition, it has been found that the hardness of the water used in rinse cycle fabric softening does not influence the softening effect. However, it is of advantage for the water to have a certain minimum hardness. Thus, hardnesses of at least 5° dH and, more particularly, in the range from about 8 to 30° dH or higher are particularly suitable for initiating the desired softening effects.

The use of the active substances or mixtures of active substances according to the invention for fabric softening is not affected by the degree of dryness of the textile material to be treated. Suitable textile materials for softening in accordance with the invention include both cotton, polyacrylonitrile, polyester and polyester/cotton blends and also linen, silk and other natural fabrics. The desired softening effect is obtained both in wet fabrics and in dry fabrics. The mixtures of active substances according to the invention are absorbed by the corresponding textile both from aqueous liquors and by forced application. The quality of feel is not directly comparable with the results hitherto obtained in practice. Fabrics treated with the mixtures according to the invention are found to be pleasantly dry and, at the same time, very soft.

EXAMPLES

General Procedure for the Alkoxylation of Thiodiglycol

Example 1

Reaction of Thiodiglycol with Ethylene Oxide (1:2)

4.0 g of a 30% by weight solution of potassium hydroxide in methanol were added to 611 g thiodiglycol (Glyezin A, a product of BASF) and heated in an autoclave to 80° C. The traces of methanol present were removed at that temperature by evacuation and purging with nitrogen five times. After the reaction temperature had been increased to 145° C., a total of 440 g ethylene oxide was added in portions so that the pressure in the reactor did not exceed a value of $5 \cdot 10^5$ Pa. On completion of the reaction, the reaction mixture was cooled to around 90° C. and traces of ethylene oxide still present were removed by evacuation. 1051 g thiodiglycol · 2 EO were obtained in the form of a light brown, clear liquid having an OH value of 530.

EXAMPLE 2

Reaction of Thiodiglycol with Ethylene Oxide (1:4)

489.g thiodiglycol were reacted with 704 g ethylene oxide as in Example 1. 1197 g thiodiglycol · 4 EO were obtained in the form of a light brown, clear product having an OH value of 407.

EXAMPLE 3

Reaction of Thiodiglycol with Ethylene Oxide (1:1)

750 g thiodiglycol were reacted with 270 g ethylene oxide as in Example 1. 1027 g thiodiglycol · 1 EO were obtained in the form of a light brown, clear product having an OH value of 623.

EXAMPLE 4

Reaction of Thiodiglycol with Ethylene Oxide (1:15)

183 g thiodiglycol were reacted with 990 g ethylene oxide as in Example 1. 1176 g thiodiglycol · 15 EO were obtained in the form of a light brown, clear product having an OH value of 178.

General procedure for the reaction of thiodiglycol alkoxylates with α-olefin epoxides and their oxidation to the sulfoxide or sulfone.

EXAMPLE 5

Reaction of thiodiglycol · 2 EO with 1-hexadecene oxide 886.9 g 1-hexadecene oxide (epoxide oxygen content: 6.21%) and 315.3 g thiodiglycol · 2 EO (from Example 1) were introduced into a reaction vessel with 7.8 g of a 50% potassium hydroxide solution and the traces of water present were removed by heating in vacuo to 100° C. The mixture, which shows a slightly exothermic reaction, was then heated under nitrogen to around 160 to 170° C. In order to monitor the reaction, the epoxide oxygen content of the reaction mixture was determined at regular intervals, an epoxide oxygen content below 0.3% being reached after a reaction time of 3 to 6 hours which indicated that the reaction was complete. After cooling, the product was neutralized with an equivalent quantity of 90% lactic acid.

EXAMPLE 6

Oxidation of the Compound of Example 5 to the Sulfone 1100 g of the reaction product of thiodiglycol · 2 EO with 1-hexadecene oxide (from Example 5) were heated to 80° C. and 153 g 70% hydrogen peroxide were slowly added over a period of about 60 minutes. During the further reaction, the temperature was kept below 90° C. by cooling. For after-reaction, the product was heated for 4.5 hours at 90° C. and then washed with hot water until the peroxide test in the washing water produced a negative result. The light yellow solid sulfone was then dried in vacuo at 120° C. Analytical data: OH value 149, acid value 0.9.

EXAMPLE 7

Reaction of thiodiglycol · 2 EO with 1-dodecene oxide and oxidation to the sulfone 875 g 1-dodecene oxide (epoxide oxygen content: 8.05%) were reacted with 492 g thiodiglycol · 2EO (from Example 1) as in Example 5 and oxidized with 449 g 35% hydrogen peroxide to form the sulfone as in Example 6. The end product is a yellowish solid (OH value 208, acid value 0.4). Yield 74%.

EXAMPLE 8

Reaction of Thiodiglycol · 1 EO with 1-hexadecene oxide and oxidation to the sulfone 1030 g 1-hexadecene oxide (epoxide oxygen content: 6.21%) were reacted with 360 g thiodiglycol · 1 EO (from Example 3) as in Example 5 and oxidized with 408 g 35% hydrogen peroxide to form the sulfone as in Example 6. The end product is a yellowish solid (OH value 161, acid value 0.3). Yield 75%.

EXAMPLE 9

Reaction of Thiodiglycol · 4 EO with 1-hexadecene oxide and oxidation to the sulfone 386 g 1-hexadecene oxide (epoxide oxygen content: 6.21%) were reacted with 223 g thiodiglycol · 4 EO (from Example 2) as in Example 5 and oxidized with 76.7 g 70% hydrogen peroxide to form the sulfone as in Example 6. The end product is a yellowish solid (OH value 125, acid value 0.2).

EXAMPLE 10

Reaction of Thiodiglycol 2 EO with 1-octadecene Oxide 1055 g 1-octadecene oxide (epoxide oxygen content: 5.46%) were reacted with 402.3 g thiodiglycol · 2 EO (from Example 1) as in Example 5.

EXAMPLE 11

Oxidation of the compound of Example 10 to the sultone 1450 g of the reaction product of 1-octadecene oxide and thiodiglycol · 2 EO were oxidized with 367 g hydrogen peroxide (35%) to form the sulfone as in Example 6. A yellowish solid (OH value 136, acid value 0.2) was obtained in a yield of 915 g (61% of the theoretical).

EXAMPLE 12

Oxidation of the compound of Example 10 to the sulfoxide 810 g of the reaction product of 1-octadecene oxide with thiodiglycol · 2 EO were oxidized with 223.5 g hydrogen peroxide (35%) to form the sulfoxide as in Example 6. A yellowish solid (OH value 158.1, Acid value 0.4) was obtained in a yield of 727 g (86% of the theoretical). General procedure for the reaction of thiodiglycol alkoxylates with monocarboxylic acids and their oxidation to the corresponding sulfoxide or sulfone.

Example 13

Reaction of thiodiglycol · 2 EO with stearic acid 994 g stearic acid, 391 g thiodiglycol · 2 EO (from Example 1) and 10.4 g tin grindings Were introduced into a reactor equipped with a stirrer and water separator and heated under nitrogen to 200° C. The course of the reaction was monitored through the quantity of water removed and by determination of the acid value which should be below 5 towards the end of the reaction; if necessary, more thiodiglycol · 2 EO may be added. After a reaction time of 6 hours (acid value 3.7) and cooling to 100° C., the product was filtered off under suction through Celite and dried.

EXAMPLE 14

Oxidation of the compound of Example 13 to the sulfone

The product of Example 13 was oxidized with 358 g hydrogen peroxide (35%) and 300 ml acetic acid to the sulfone in the same way as in Example 6. 1121 g of a pale yellow colored solid were obtained (saponification value 156, iodine value 1.1).

EXAMPLE 15

Reaction of thiodiglycol · 2 EO with oleio acid and oxidation to the sulfone 975 g technical grade oleic acid were reacted with 391 g thiodiglycol · 2 EO in the same way as in Example 13 and subsequently oxidized with 358 g hydrogen peroxide (35%) to the sulfone. 1136 g (84% of the theoretical) of a yellow cloudy liquid were obtained as the end product (saponification value 159, iodine value 70).

TABLE 1

Properties of water-containing mixtures of active substances based on selected sulfones or sulfoxide of alkoxylated thiodiglycol (TDG) derivatives in admixture with tallow alcohol sulfate[1] in a washing machine[2]

| Compound[3] | Feel[4] | pH Value | Appearance | Example |
|---|---|---|---|---|
| Sulfone A (of TDG · 2 EO and 1-dodecene oxide) | 2 | 9.8 | 2 Phases | 7 |
| Sulfone B (of TDG · 1 EO and 1-hexadecene oxide) | 3 | 9.7 | Stable | 8 |
| Sulfone C (of TDG · 2 EO and 1-hexadecene oxide) | 3.5 | 9.7 | Stable | 6 |
| Sulfone D (of TDG · 4 EO and 1-hexadecene oxide) | — | 9.8 | Stable | 9 |
| Sulfone E (of TDG · 2 EO and 1-octadecene oxide) | — | 10.1 | Stable | 10 |
| Sulfoxide F (of TDG · 2 EO and 1-octadecene oxide) | — | 9.9 | Stable | 12 |
| Sulfone G (of TDG · 2 EO and stearic acid) | 2 | 7.9 | Stable | 14 |
| Sulfone H (of TDG · 2 EO | — | 7.2 | 2 Phases | 15 |

TABLE 1-continued

Properties of water-containing mixtures of active substances based on selected sulfones or sulfoxide of alkoxylated thiodiglycol (TDG) derivatives in admixture with tallow alcohol sulfate[1] in a washing machine[2]

| Compound[3] | Feel[4] | pH Value | Appearance | Example |
|---|---|---|---|---|
| and oleic acid | | | | |

[1]Sulfopon T55 ® (Na tallow alcohol sulfate, 55% aqueous solution; a product of Henkel KGaA)
[2]Washing machine (Miele-W 717 ®), 60° C. wash, 210 g of an approx. 9% aqueous fabric softening mixture (5% of one of compounds A to F, 7.5% Sulfopon T 55 ® and 87.5% water); 0.3% active fabric softener (based on 3.5 kg test material), pretreatment of the test material: 5 × hardened terry swatches (washed with 215 g phosphate-free Persil ® per 3.5 kg test material at 60° C., no prewash); water hardness 16°dH
[3]Nomenclature of compounds A to F
A: bis-[2-(2-hydroxydodecyloxy)ethyl]sulfone (· 2 EO)
B: bis-[2-(2-hydroxyhexadecyloxy)ethyl]sulfone (· 1 EO)
C: bis-[2-(2-hydroxyhexadecyloxy)ethyl]sulfone (· 2 EO)
D: bis-[2-(2-hydroxyhexadecyloxy)ethyl]sulfone (· 4 EO)
E: bis-[2-(2-hydroxyoctadecyloxy)ethyl]sulfone (· 2 EO)
F: bis-[2-(2-hydroxyoctadecyloxy)ethyl]sulfoxide (· 2 EO)

[4]The feel imparted by this new N-free fabric softener could not be evaluated on the basis of "standard feels". The feel could be described as "pleasant", "dry", "light" and "soft". On applicants' conventional feel scale, the observed feel was defined as follows in accordance with modified DIN 10 954: 0 = roughest feel (no softener) 4 = softest feel

TABLE 2

Properties of aqueous mixtures of active substances based on selected sulfones or sulfoxides of alkoxylated thiodiglycol (TDG) derivatives in admixture with tallow alcohol sulfate[1] after pH adjustment with citric acid in a Wacker machine[2]

| Compound[3] | Feel[4] | pH Value | Appearance | Example |
|---|---|---|---|---|
| Sulfone A (of TDG · 2 EO and 1-dodecene oxide) | 1 | 5.2 | Deposit | 7 |
| Sulfone B (of TDG · 1 EO and 1-hexadecene oxide) | 3.8 | 5.2 | Stable | 8 |
| Sulfone C (of TDG · 2 EO and 1-hexadecene oxide) | 3.5 | 5.2 | Stable | 6 |
| Sulfone D (of TDG · 4 EO and 1-hexadecene oxide) | — | 5.2 | Stable | 9 |
| Sulfone E (of TDG · 2 EO and 1-octadecene oxide) | 1.5 | 5.2 | Stable | 10 |
| Sulfoxide F (of TDG · 2 EO and 1-octadecene oxide) | 2.8 | 5.2 | Stable | 12 |
| Sulfone G (of TDG · 2 EO and stearic acid) | 3 | 5.2 | Stable | 14 |
| Sulfone H (of TDG · 2 EO and oleic acid) | — | 5.2 | 2 Phases | 15 |

TABLE 2-continued

Properties of aqueous mixtures of active substances based on selected sulfones or sulfoxides of alkoxylated thiodiglycol (TDG) derivatives in admixture with tallow alcohol sulfate[1] after pH adjustment with citric acid in a Wacker machine[2]

| Compound[3] | Feel[4] | pH Value | Appearance | Example |
|---|---|---|---|---|
| and oleic acid | | | | |

[1]Sulfopon T55 ® (Na tallow alcohol sulfate, 55% aqueous solution; a product of Henkel KGaA)
[2]Wacker machine; liquor ratio 1:10; 3.6 g of an approx. 9% aqueous fabric softening mixture (5% of one of compounds A to F, 7.5% Sulfopon T 55 ® and 87.5% water); 0.3% active fabric softener (based on 60 g test material), 5 mins. treatment time, pretreatment of the test material: 5 × hardened terry swatches (washed with 215 g phosphate-free Persil ® per 3.5 kg test material at 60° C., no prewash); water hardness 16°dH
[3]Nomenclature of compounds A to F
A: bis-[2-(2-hydroxydodecyloxy)ethyl]sulfone (· 2 EO)
B: bis-[2-(2-hydroxyhexadecyloxy)ethyl]sulfone (· 1 EO)
C: bis-[2-(2-hydroxyhexadecyloxy)ethyl]sulfone (· 2 EO)
D: bis-[2-(2-hydroxyhexadecyloxy)ethyl]sulfone (· 4 EO)
E: bis-[2-(2-hydroxyoctadecyloxy)ethyl]sulfone (· 2 EO)
F: bis-[2-(2-hydroxyoctadecyloxy)ethyl]sulfoxide (· 2 EO)

[4]The feel imparted by this new N-free fabric softener could not be evaluated on the basis of "standard feels". The feel could be described as "pleasant", "dry", "light" and "soft". On applicants' conventional feel scale, the observed feel was defined as follows in accordance with modified DIN 10 954: 0 = roughest feel (no softener) 4 = softest feel

We claim:

1. A fabric-softening composition comprising (a) alkoxylated thiodiglycol sulfoxide derivataives or thiodiglycol sulfone derivatives corresponding to formula I

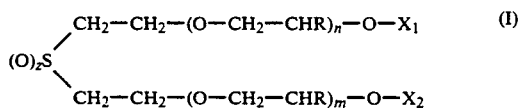

wherein $X_1$ and $X_2$ may be the same or different and represent a hydroxyl-substituted alkyl radical containing 8 to 30 carbon atoms, an acyl radical of an alkyl monocarboxylic acid containing 8 to 30 carbon atoms, and $X_1$ or $X_2$ may be hydrogen, R represents hydrogen or methyl, z is 1 to 2, n is 0 to 25 and m is 1 to 25 and (b) an anionic or nonionic surfactant or mixtures thereof.

2. A composition as in claim 1 in the form of an aqueous solution.

3. A composition as in claim 1 wherein said derivatives are present in a quantity of from about 5 to about 95% /wt, based on the weight of said composition.

4. A composition as in claim 1 wherein said anionic surfactant is selected from the group consisting of a fatty alcohol sulfate and an alkyl sulfonate.

5. A composition as in claim 1 wherein said nonionic surfactant comprises an alkyl glycoside.

6. A composition as in claim 1 further comprising an emulsifying agent selected from the group consisting of a glycerol partial ether and a glycerol partial ester.

* * * * *